United States Patent
Donhowe et al.

(10) Patent No.: US 11,871,898 B2
(45) Date of Patent: Jan. 16, 2024

(54) SYSTEMS AND METHODS FOR INTERVENTIONAL PROCEDURE PLANNING

(71) Applicant: INTUITIVE SURGICAL OPERATIONS, INC., Sunnyvale, CA (US)

(72) Inventors: Caitlin Q. Donhowe, Mountain View, CA (US); Prashant Chopra, Foster City, CA (US); Dorin Panescu, San Jose, CA (US); Carol Reiley, Mountain View, CA (US); Tao Zhao, Sunnyvale, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

(21) Appl. No.: 17/867,212

(22) Filed: Jul. 18, 2022

(65) Prior Publication Data
US 2022/0346751 A1  Nov. 3, 2022

Related U.S. Application Data

(63) Continuation of application No. 16/751,797, filed on Jan. 24, 2020, now Pat. No. 11,426,141, which is a (Continued)

(51) Int. Cl.
*A61B 34/10* (2016.01)
*A61B 8/12* (2006.01)
(Continued)

(52) U.S. Cl.
CPC ............... *A61B 8/12* (2013.01); *A61B 8/085* (2013.01); *A61B 8/0841* (2013.01);
(Continued)

(58) Field of Classification Search
CPC ......... A61B 8/12; A61B 8/0841; A61B 8/085; A61B 8/4263; A61B 10/04;
(Continued)

(56) References Cited

U.S. PATENT DOCUMENTS

| 5,740,808 | A | 4/1998 | Panescu et al. |
| 5,999,837 | A | 12/1999 | Messner et al. |

(Continued)

FOREIGN PATENT DOCUMENTS

| CN | 1986015 A | 6/2007 |
| CN | 101375805 A | 3/2009 |

(Continued)

OTHER PUBLICATIONS

Wen et al. Robot-Assissted RF Ablation With Interactive Planning and Mixed Reality Guidance 2012 IEEE/SICE International Symposium on System Integration, Dec. 16, 2012 (Year: 2012).*

(Continued)

*Primary Examiner* — Rehana Perveen
*Assistant Examiner* — Cuong V Luu
(74) *Attorney, Agent, or Firm* — Haynes & Boone, LLP.

(57) ABSTRACT

A system for performing an interventional procedure includes an interventional instrument and a control system. The instrument includes a catheter and an interventional tool extendable from the catheter. The control system includes a processor and a memory comprising machine-readable instructions that cause the control system to: receive a model of an anatomic structure, the anatomic structure including a plurality of passageways; identify a target structure in the model; receive information about a maximum extension length the interventional tool can be extended relative to a distal tip of the catheter; based upon the received information about the maximum extension length, identify a planned deployment location for positioning the distal tip of the (Continued)

catheter to perform the interventional procedure on the target structure; determine a navigational path for the catheter to the target structure; and navigate the catheter to the identified planned deployment location via computer control or based on user input.

21 Claims, 7 Drawing Sheets

Related U.S. Application Data continuation of application No. 16/247,057, filed on Jan. 14, 2019, now Pat. No. 10,582,909, which is a continuation of application No. 14/144,232, filed on Dec. 30, 2013, now abandoned.

(60) Provisional application No. 61/747,920, filed on Dec. 31, 2012.

(51) Int. Cl.
| | | |
|---|---|---|
| *A61B 8/00* | (2006.01) | |
| *A61B 8/08* | (2006.01) | |
| *A61B 10/04* | (2006.01) | |
| *A61B 17/00* | (2006.01) | |
| A61B 5/06 | (2006.01) | |
| A61B 90/00 | (2016.01) | |
| A61B 34/20 | (2016.01) | |
| A61B 5/00 | (2006.01) | |

(52) U.S. Cl.
CPC ............ *A61B 8/4263* (2013.01); *A61B 10/04* (2013.01); *A61B 17/00234* (2013.01); *A61B 34/10* (2016.02); *A61B 5/0066* (2013.01); *A61B 5/065* (2013.01); *A61B 8/4245* (2013.01); *A61B 2034/102* (2016.02); *A61B 2034/107* (2016.02); *A61B 2034/2051* (2016.02); *A61B 2090/364* (2016.02)

(58) Field of Classification Search
CPC . A61B 17/00234; A61B 34/10; A61B 5/0066; A61B 5/065; A61B 8/4245; A61B 2090/364
See application file for complete search history.

(56) References Cited

U.S. PATENT DOCUMENTS

| | | | |
|---|---|---|---|
| 6,083,170 A | 7/2000 | Ben-Haim | |
| 6,380,732 B1 | 4/2002 | Gilboa | |
| 6,389,187 B1 | 5/2002 | Greenaway et al. | |
| 6,468,265 B1 | 10/2002 | Evans et al. | |
| 7,206,462 B1 | 4/2007 | Betke et al. | |
| 7,506,650 B2 | 3/2009 | Lowe et al. | |
| 7,725,214 B2 | 5/2010 | Diolaiti | |
| 7,772,541 B2 | 8/2010 | Froggatt et al. | |
| 7,781,724 B2 | 8/2010 | Childers et al. | |
| 7,930,065 B2 | 4/2011 | Larkin et al. | |
| 8,062,212 B2 | 11/2011 | Belson | |
| 8,226,546 B2 | 7/2012 | Belson | |
| 8,248,414 B2 | 8/2012 | Gattani et al. | |
| 8,303,505 B2 | 11/2012 | Webler et al. | |
| 8,317,746 B2 | 11/2012 | Sewell et al. | |
| 8,361,090 B2 | 1/2013 | Belson | |
| 8,398,541 B2 | 3/2013 | Dimaio et al. | |
| 8,517,923 B2 | 8/2013 | Belson et al. | |
| 8,611,983 B2 | 12/2013 | Glossop et al. | |
| 9,289,268 B2 | 3/2016 | Ramraj et al. | |
| 10,582,909 B2 | 3/2020 | Donhowe et al. | |
| 10,588,597 B2 | 3/2020 | Zhao et al. | |
| 2002/0077544 A1 | 6/2002 | Shahidi | |
| 2002/0115941 A1 | 8/2002 | Whayne et al. | |
| 2002/0133057 A1 | 9/2002 | Kukuk | |
| 2003/0085890 A1 | 5/2003 | Baumberg et al. | |
| 2003/0093067 A1 | 5/2003 | Panescu | |
| 2003/0163142 A1 | 8/2003 | Paltieli et al. | |
| 2004/0068187 A1 | 4/2004 | Krause et al. | |
| 2004/0254458 A1 | 12/2004 | Govari | |
| 2005/0020901 A1* | 1/2005 | Belson ............... | G02B 23/2476 600/407 |
| 2005/0182295 A1 | 8/2005 | Soper et al. | |
| 2006/0013523 A1 | 1/2006 | Childlers et al. | |
| 2006/0025677 A1 | 2/2006 | Verard et al. | |
| 2006/0184016 A1* | 8/2006 | Glossop ............... | A61B 1/2676 600/434 |
| 2006/0239544 A1 | 10/2006 | Yankelevitz et al. | |
| 2007/0237373 A1 | 10/2007 | Kiraly et al. | |
| 2007/0249911 A1 | 10/2007 | Simon | |
| 2007/0293734 A1 | 12/2007 | Coste-Maniere et al. | |
| 2008/0082109 A1 | 4/2008 | Moll et al. | |
| 2008/0123922 A1 | 5/2008 | Gielen et al. | |
| 2008/0255505 A1 | 10/2008 | Carlson et al. | |
| 2008/0287803 A1 | 11/2008 | Li et al. | |
| 2008/0287805 A1 | 11/2008 | Li | |
| 2008/0294034 A1 | 11/2008 | Krueger et al. | |
| 2009/0062813 A1 | 3/2009 | Prisco et al. | |
| 2009/0088632 A1 | 4/2009 | Khamene et al. | |
| 2009/0156895 A1 | 6/2009 | Higgins et al. | |
| 2009/0163810 A1 | 6/2009 | Kanade et al. | |
| 2009/0171184 A1* | 7/2009 | Jenkins ............... | G01R 33/3415 606/130 |
| 2009/0227861 A1 | 9/2009 | Ganatra et al. | |
| 2009/0262980 A1 | 10/2009 | Markowitz et al. | |
| 2009/0268010 A1 | 10/2009 | Zhao et al. | |
| 2010/0249506 A1 | 9/2010 | Prisco | |
| 2011/0112569 A1 | 5/2011 | Friedman et al. | |
| 2011/0207997 A1 | 8/2011 | Greenburg et al. | |
| 2011/0282140 A1 | 11/2011 | Itkowitz et al. | |
| 2012/0004533 A1 | 1/2012 | Peng et al. | |
| 2012/0035438 A1 | 2/2012 | Ferren et al. | |
| 2012/0059378 A1* | 3/2012 | Farrell ................. | A61B 90/25 606/80 |
| 2012/0065481 A1 | 3/2012 | Hunter et al. | |
| 2012/0203067 A1 | 8/2012 | Higgins et al. | |
| 2012/0289777 A1 | 11/2012 | Chopra et al. | |
| 2012/0289843 A1 | 11/2012 | Chopra et al. | |
| 2012/0296620 A1 | 11/2012 | Aulbach | |
| 2012/0327204 A1 | 12/2012 | Friedman et al. | |
| 2012/0330622 A1 | 12/2012 | Butson et al. | |
| 2013/0030408 A1 | 1/2013 | Piferi et al. | |
| 2013/0085774 A1 | 4/2013 | Chen et al. | |
| 2013/0303876 A1* | 11/2013 | Gelfand ................ | A61B 18/00 600/407 |
| 2014/0188440 A1 | 7/2014 | Donhowe et al. | |
| 2015/0094914 A1 | 4/2015 | Abreu | |
| 2015/0173619 A1* | 6/2015 | Zvuloni ............. | A61B 10/0275 600/425 |
| 2015/0221105 A1 | 8/2015 | Tripathi et al. | |
| 2015/0347682 A1 | 12/2015 | Chen et al. | |
| 2017/0132812 A1 | 5/2017 | Tripathi et al. | |
| 2020/0155116 A1 | 5/2020 | Donhowe et al. | |
| 2020/0214664 A1 | 7/2020 | Zhao et al. | |

FOREIGN PATENT DOCUMENTS

| | | |
|---|---|---|
| CN | 101420898 A | 4/2009 |
| CN | 100515332 C | 7/2009 |
| CN | 101862205 A | 10/2010 |
| CN | 102186404 A | 9/2011 |
| CN | 102406517 A | 4/2012 |
| CN | 102481115 A | 5/2012 |
| CN | 102740755 A | 10/2012 |
| CN | 102740791 A | 10/2012 |
| DE | 202005016721 U1 | 3/2007 |
| DE | 102007009016 A1 | 8/2008 |
| EP | 1481637 A1 | 12/2004 |
| EP | 1779802 A2 | 5/2007 |
| EP | 2238901 A2 | 10/2010 |
| EP | 2377457 A1 | 10/2011 |
| JP | 2009542374 A | 12/2009 |

(56) References Cited

FOREIGN PATENT DOCUMENTS

| | | |
|---|---|---|
| JP | 2010540021 A | 12/2010 |
| JP | 2011525827 A | 9/2011 |
| JP | 2012510332 A | 5/2012 |
| WO | WO-2005072445 A2 | 8/2005 |
| WO | WO-2005082246 A1 | 9/2005 |
| WO | WO-2006124388 A1 | 11/2006 |
| WO | WO-2009023801 A1 | 2/2009 |
| WO | WO-2010049834 A1 | 5/2010 |
| WO | WO-2010064154 A1 | 6/2010 |
| WO | WO-2010078009 A1 | 7/2010 |
| WO | WO-2011057157 A1 | 5/2011 |
| WO | WO-2012158324 A2 | 11/2012 |
| WO | WO-2014106253 A1 | 7/2014 |

OTHER PUBLICATIONS

Yaniv et al. Needle-Based Interventions With the Image-Guided Surgery Toolkit (IGSTK): From Phantoms to Clinical Trials IEEE Transactions on Biomedical Engineering vol. 57, No. 4, Apr. 2010 (Year: 2010).*

Dagon, B. et al., "Real-Time Update of 3D Deformable Models for Computer Aided Liver Surgery," IEEE, 2008, 4 pages.

Extended European Search Report for Application No. 13867391.8, dated Jul. 22, 2016, 7 pages.

Extended European Search Report for Application No. 13868283.8, dated Jul. 26, 2016, 7 pages.

Extended European Search Report for Application No. 18188100.4, dated Nov. 13, 2018, 8 pages.

International Search Report and Written Opinion for Application No. PCT/US13/78497, dated Apr. 28, 2014, 14 pages.

International Search Report and Written Opinion for Application No. PCT/US13/78508, dated Apr. 3, 2014, 15 pages.

Linte, C.A. et al., "Evaluation of Model-Enhanced Ultrasound-Assisted Interventional Guidance in a Cardiac Phantom," IEEE Transactions on Biomedical Engineering, Sep. 2010, vol. 57 (9), pp. 2209-2218.

Office Action dated Dec. 28, 2016 for Chinese Application No. 201380068398.6 filed Dec. 31, 2013, 18 pages.

Tovar-Arrisga S., et al., "A Fully Sensorized Cooperative Robotic System for Surgical Interventions Sensors," Sensors (Basel), Jul. 9, 2012, vol. 12 (7), pp.9423-9447.

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

Wen r., et al., "Robot-Assisted RF Ablation with Interactive Planning and Mixed Reality Guidance," IEEE/SICE International Symposium on System Integration, 2012, pp. 31-36.

Yaniv Z., et al., "Needle-Based Interventions With the Image-Guided Surgery Toolkit (IGSTK): From Phantoms to Clinical Trials," IEEE Transactions on Biomedical Engineering, 2010, vol. 57 (4), pp. 922-933.

\* cited by examiner

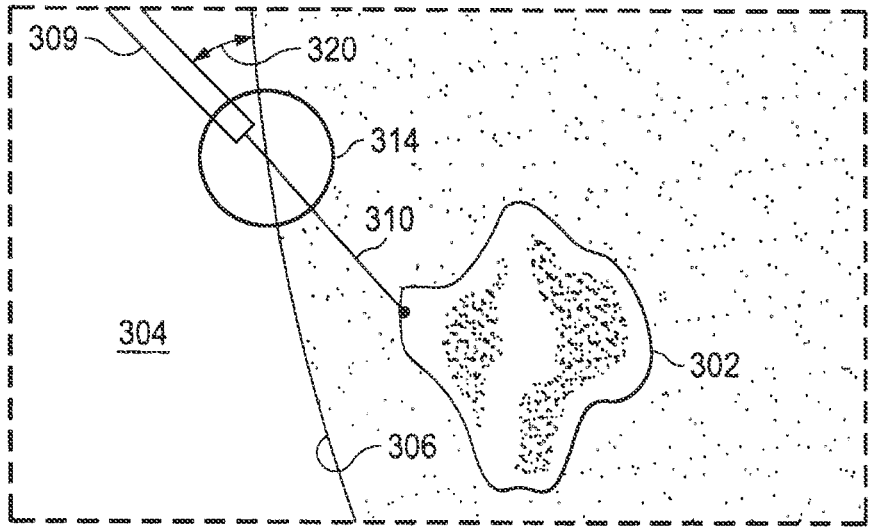
Fig. 5
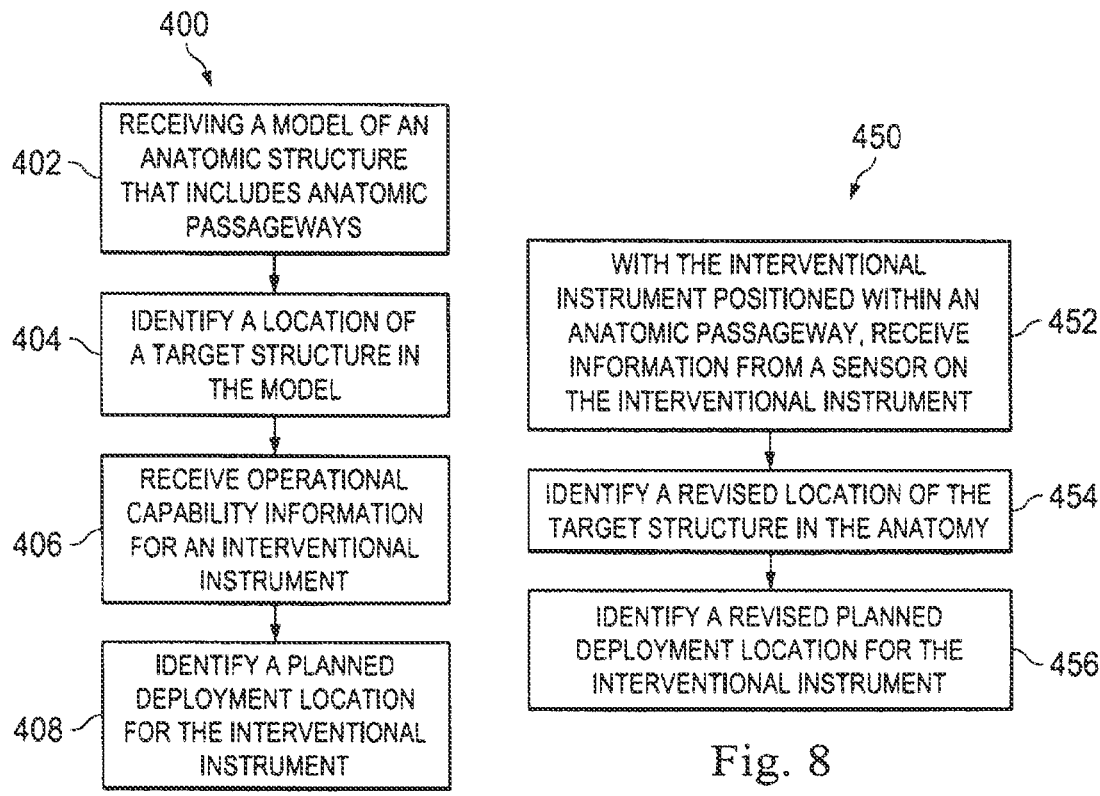
Fig. 7
Fig. 8

SYSTEMS AND METHODS FOR INTERVENTIONAL PROCEDURE PLANNING

CROSS-REFERENCE TO RELATED APPLICATIONS

This application is a continuation of U.S. patent application Ser. No. 16/751,797, filed Jan. 24, 2020 which is a continuation of U.S. patent application Ser. No. 16/247,057, filed Jan. 14, 2019, which is a continuation of U.S. patent application Ser. No. 14/144,232, filed Dec. 30, 2013, which claims the benefit of U.S. Provisional Application No. 61/747,920, filed Dec. 31, 2012, all of which are incorporated by reference in their entirety.

FIELD

The present disclosure is directed to systems and methods for navigating a patient anatomy to conduct a minimally invasive procedure, and more particularly to systems and methods for planning a procedure to deploy an interventional instrument.

BACKGROUND

Minimally invasive medical techniques are intended to reduce the amount of tissue that is damaged during interventional procedures, thereby reducing patient recovery time, discomfort, and deleterious side effects. Such minimally invasive techniques may be performed through natural orifices in a patient anatomy or through one or more surgical incisions. Through these natural orifices or incisions clinicians may insert interventional instruments (including surgical, diagnostic, therapeutic, or biopsy instruments) to reach a target tissue location. To reach the target tissue location, a minimally invasive interventional instrument may navigate natural or surgically created passageways in anatomical systems such as the lungs, the colon, the intestines, the kidneys, the heart, the circulatory system, or the like. To assist the clinician in navigating the instrument through the passageways, models of the passageway are prepared using pre-operative or inter-operative imaging. Current systems for deploying an interventional instrument identify an instrument deployment location as the point within the modeled passageways closest to the target tissue location. This closest-point deployment location may be difficult to access given the constraints of the interventional instrument or the anatomy. Improved systems and methods are needed to determine a planned instrument deployment location for conducting a procedure on the target tissue location.

SUMMARY

The embodiments of the invention are summarized by the claims that follow the description.

In one embodiment, a method of planning a procedure to deploy an interventional instrument comprises receiving a model of an anatomic structure. The anatomic structure includes a plurality of passageways. The method further includes identifying a target structure in the model and receiving information about an operational capability of the interventional instrument within the plurality of passageways. The method further comprises identifying a planned deployment location for positioning a distal tip of the interventional instrument to perform the procedure on the target structure based upon the operational capability of the interventional instrument.

In another embodiment, a system comprises a non-transitory computer readable media containing computer executable instructions for planning a procedure to deploy an interventional instrument. The computer executable instructions include instructions for receiving a model of an anatomic structure including a plurality of passageways and instructions for identifying a target structure in the model. The computer executable instructions also include instructions for receiving information about an operational capability of the interventional instrument within the plurality of passageways and instructions for identifying a planned deployment location for positioning a distal tip of the interventional instrument to perform the procedure on the target structure based upon the operational capability of the interventional instrument.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

FIG. 5 is a view of a portion of the FIG. 4.

FIG. 7 is a flowchart describing a method for identifying a planned deployment location for an interventional instrument.

FIG. 8 is a flowchart describing a method for revising the planned deployment location based upon sensor feedback.

Figure 9:
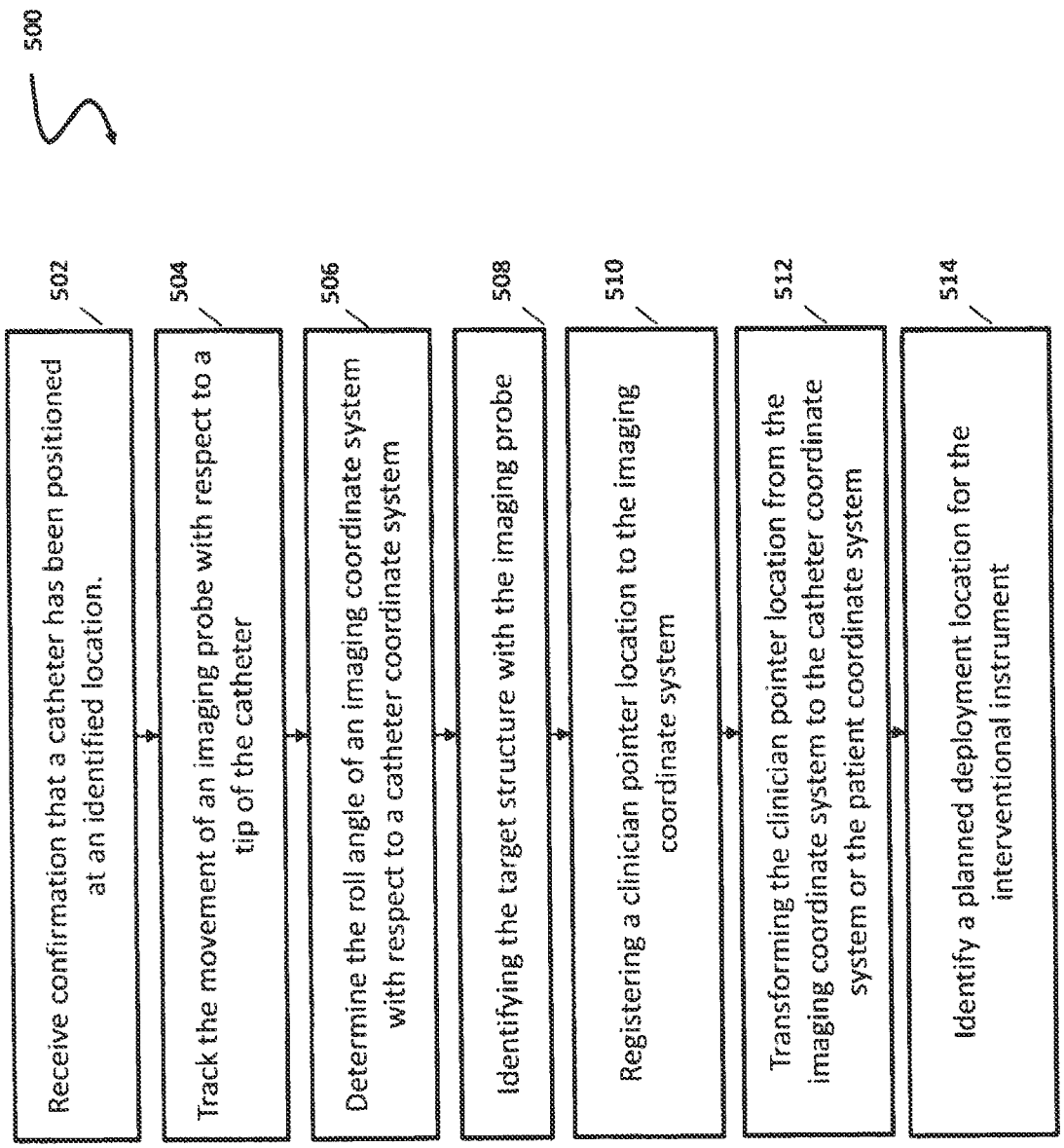
FIG. 9 is a flowchart describing a method for identifying the target structure using the imaging systems.
Figure 10A:
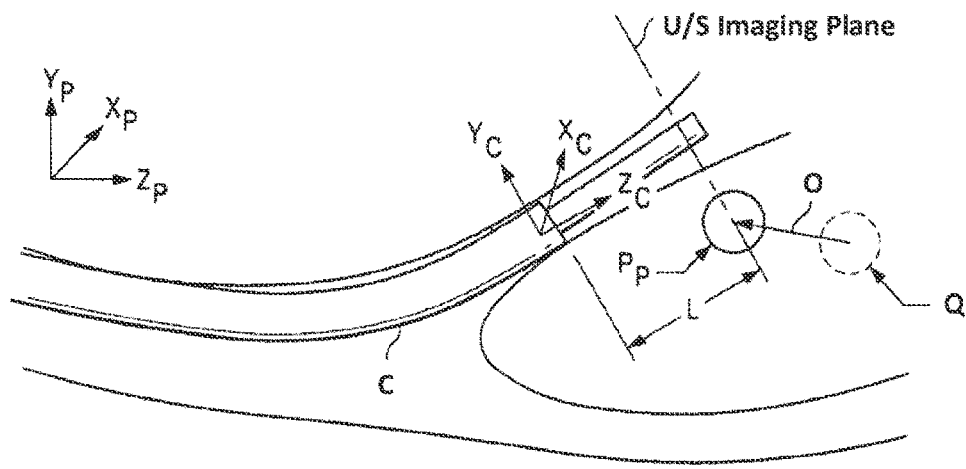
Figure 10B:
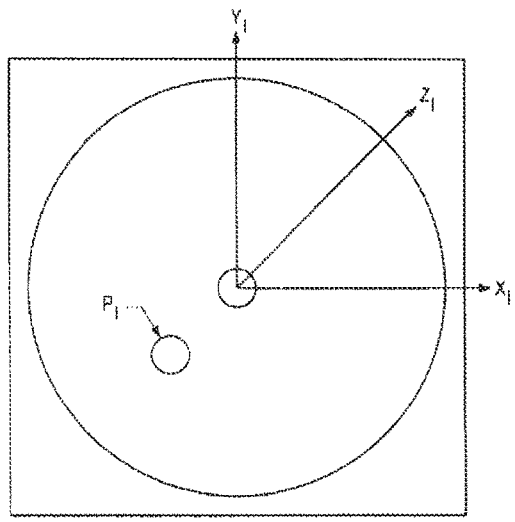
Figure 11:
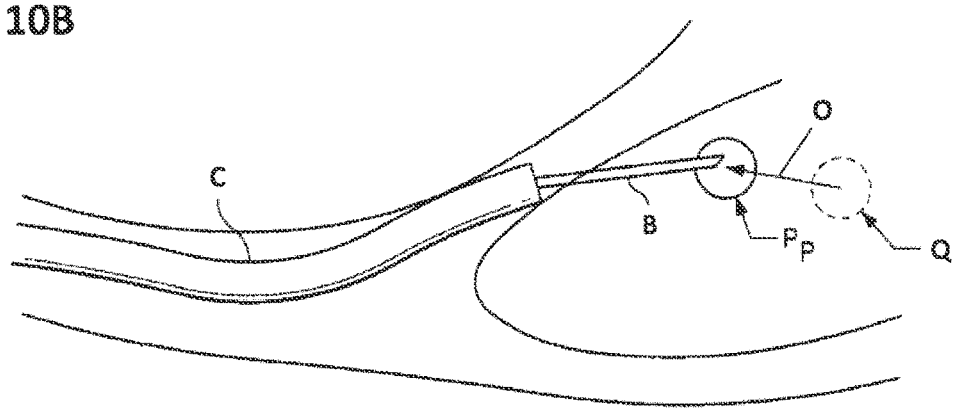

FIGS. 10A, 10B, and 11 are illustrations of the method of FIG. 9.

DETAILED DESCRIPTION

In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention. And, to avoid needless descriptive repetition, one or more components or actions described in accordance with one illustrative embodiment can be used or omitted as applicable from other illustrative embodiments.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Figure 1:
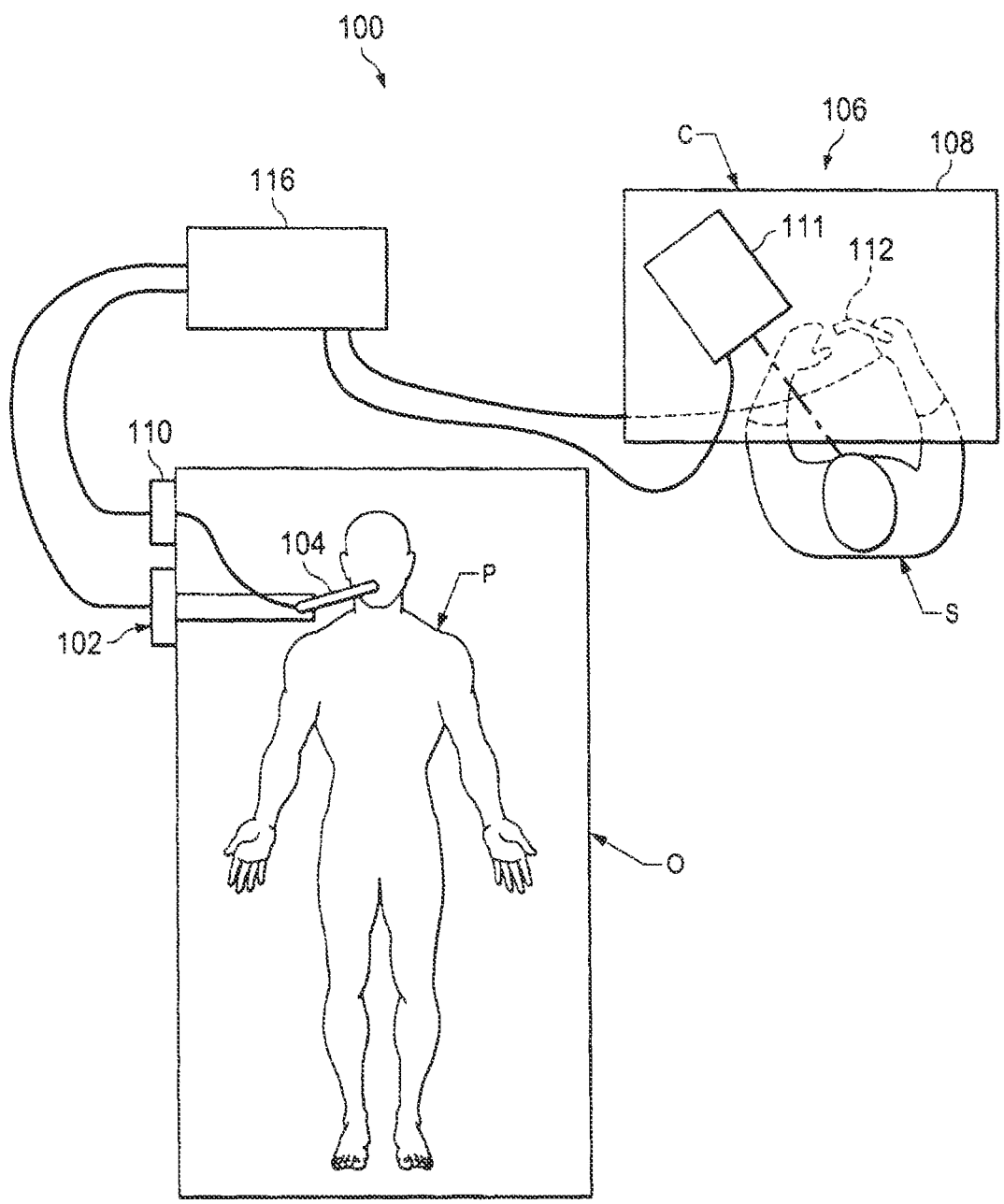
FIG. 1 is a teleoperated interventional system, in accordance with embodiments of the present disclosure.

Referring to FIG. 1 of the drawings, a teleoperated interventional system for use in, for example, surgical, diagnostic, therapeutic, or biopsy procedures, is generally indicated by the reference numeral 100. As shown in FIG. 1, the teleoperated system 100 generally includes an interventional manipulator assembly 102 for operating an interventional instrument 104 in performing various procedures on the patient P. The assembly 102 is mounted to or near an operating table O. A master assembly 106 allows the surgeon S to view the surgical site and to control the slave manipulator assembly 102.

The master assembly 106 may be located at a surgeon's console C which is usually located in the same room as operating table O. However, it should be understood that the surgeon S can be located in a different room or a completely different building from the patient P. Master assembly 106 generally includes an optional support 108 and one or more control device(s) 112 for controlling the manipulator assemblies 102. The control device(s) 112 may include any number of a variety of input devices, such as joysticks, trackballs, data gloves, trigger-guns, hand-operated controllers, voice recognition devices, body motion or presence sensors, or the like. In some embodiments, the control device(s) 112 will be provided with the same degrees of freedom as the associated interventional instruments 104 to provide the surgeon with telepresence, or the perception that the control device(s) 112 are integral with the instruments 104 so that the surgeon has a strong sense of directly controlling instruments 104. In other embodiments, the control device(s) 112 may have more or fewer degrees of freedom than the associated interventional instruments 104 and still provide the surgeon with telepresence. In some embodiments, the control device(s) 112 are manual input devices which move with six degrees of freedom, and which may also include an actuatable handle for actuating instruments (for example, for closing grasping jaws, applying an electrical potential to an electrode, delivering a medicinal treatment, or the like).

In alternative embodiments, the teleoperated system may include more than one slave manipulator assembly and/or more than one master assembly. The exact number of manipulator assemblies will depend on the surgical procedure and the space constraints within the operating room, among other factors. The master assemblies may be collocated, or they may be positioned in separate locations. Multiple master assemblies allow more than one operator to control one or more slave manipulator assemblies in various combinations.

An optional visualization system 110 may include an endoscope system such that a concurrent (real-time) image of the surgical site is provided to surgeon console C. The concurrent image may be, for example, a two- or three-dimensional image captured by an endoscopic probe positioned within the surgical site. In this embodiment, the visualization system 110 includes endoscopic components that may be integrally or removably coupled to the interventional instrument 104. In alternative embodiments, however, a separate endoscope attached to a separate manipulator assembly may be used to image the surgical site. Alternatively, a separate endoscope assembly may be directly operated by a user, without teleoperational control. The endoscope assembly may include active steering (e.g., via teleoperated steering wires) or passive steering (e.g., via guide wires or direct user guidance). The visualization system 110 may be implemented as hardware, firmware, software, or a combination thereof, which interacts with or is otherwise executed by one or more computer processors, which may include the processor(s) of a control system 116.

A display system 111 may display an image of the surgical site and interventional instruments captured by the visualization system 110. The display 111 and the master control device(s) 112 may be oriented such that the relative positions of the imaging device in the scope assembly and the interventional instruments are similar to the relative positions of the surgeon's eyes and hand(s) so the operator can manipulate the interventional instrument 104 and the master control device(s) 112 as if viewing the workspace in substantially true presence. True presence means that the displayed tissue image appears to an operator as if the operator was physically present at the imager location and directly viewing the tissue from the imager's perspective.

Alternatively or additionally, display system 111 may present images of the surgical site recorded and/or modeled preoperatively using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, or the like. The presented preoperative images may include two-dimensional, three-dimensional, or four-dimensional (including e.g., time based or velocity based information) images.

In some embodiments, the display system 111 may display a virtual visualization image in which the actual location of the interventional instrument is registered (e.g., dynamically referenced) with preoperative or concurrent images from the modeled anatomy to present the surgeon S with a virtual image of the internal surgical site at the location of the tip of the surgical instrument.

In other embodiments, the display system 111 may display a virtual visualization image in which the actual location of the interventional instrument is registered with prior images (including preoperatively recorded images) or concurrent images from the modeled anatomy to present the surgeon S with a virtual image of an interventional instrument at the surgical site. An image of a portion of the interventional instrument may be superimposed on the virtual image to assist the surgeon controlling the interventional instrument.

In FIG. 1, a control system 116 includes at least one processor (not shown), and typically a plurality of processors, for effecting control between the slave surgical manipulator assembly 102, the master assembly 106, the visualization system 110, and the display system 11. The control system 116 also includes programmed instructions (e.g., a computer-readable medium storing the instructions)

to implement some or all of the methods described herein. While control system 116 is shown as a single block in the simplified schematic of FIG. 1, the system may comprise a number of data processing circuits (e.g., on the slave surgical manipulator assembly 102 and/or on the master assembly 106), with at least a portion of the processing optionally being performed adjacent the slave surgical manipulator assembly, a portion being performed at the master assembly, and the like. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 116 supports wireless communication protocols such as Bluetooth, IrDA, HomeRF, IEEE 802.11. DECT, and Wireless Telemetry.

In some embodiments, control system 116 may include one or more servo controllers to provide force and torque feedback from the interventional instruments 104 to one or more corresponding servomotors for the control device(s) 112. The servo controller(s) may also transmit signals instructing manipulator assembly 102 to move instruments which extend into an internal surgical site within the patient body via openings in the body. Any suitable conventional or specialized servo controller may be used. A servo controller may be separate from, or integrated with, manipulator assembly 102. In some embodiments, the servo controller and manipulator assembly are provided as part of a manipulator arm cart positioned adjacent to the patient's body.

Each manipulator assembly 102 supports a interventional instrument 104 and may comprise a kinematic structure of one or more non-servo controlled links (e.g., one or more links that may be manually positioned and locked in place, generally referred to as a set-up structure) and a teleoperated manipulator. The teleoperated manipulator assembly 102 is driven by a plurality of actuators (e.g., motors). These motors actively move the teleoperated manipulators in response to commands from the control system 116. The motors are further coupled to the interventional instrument so as to advance the interventional instrument into a naturally or surgically created anatomical orifice and to move the distal end of the interventional instrument in multiple degrees of freedom, which may include three degrees of linear motion (e.g., linear motion along the X, Y, Z Cartesian axes) and three degrees of rotational motion (e.g., rotation about the X, Y, Z Cartesian axes). Additionally, the motors can be used to actuate an articulable end effector of the instrument for grasping tissue in the jaws of a biopsy device or the like.

Figure 2:
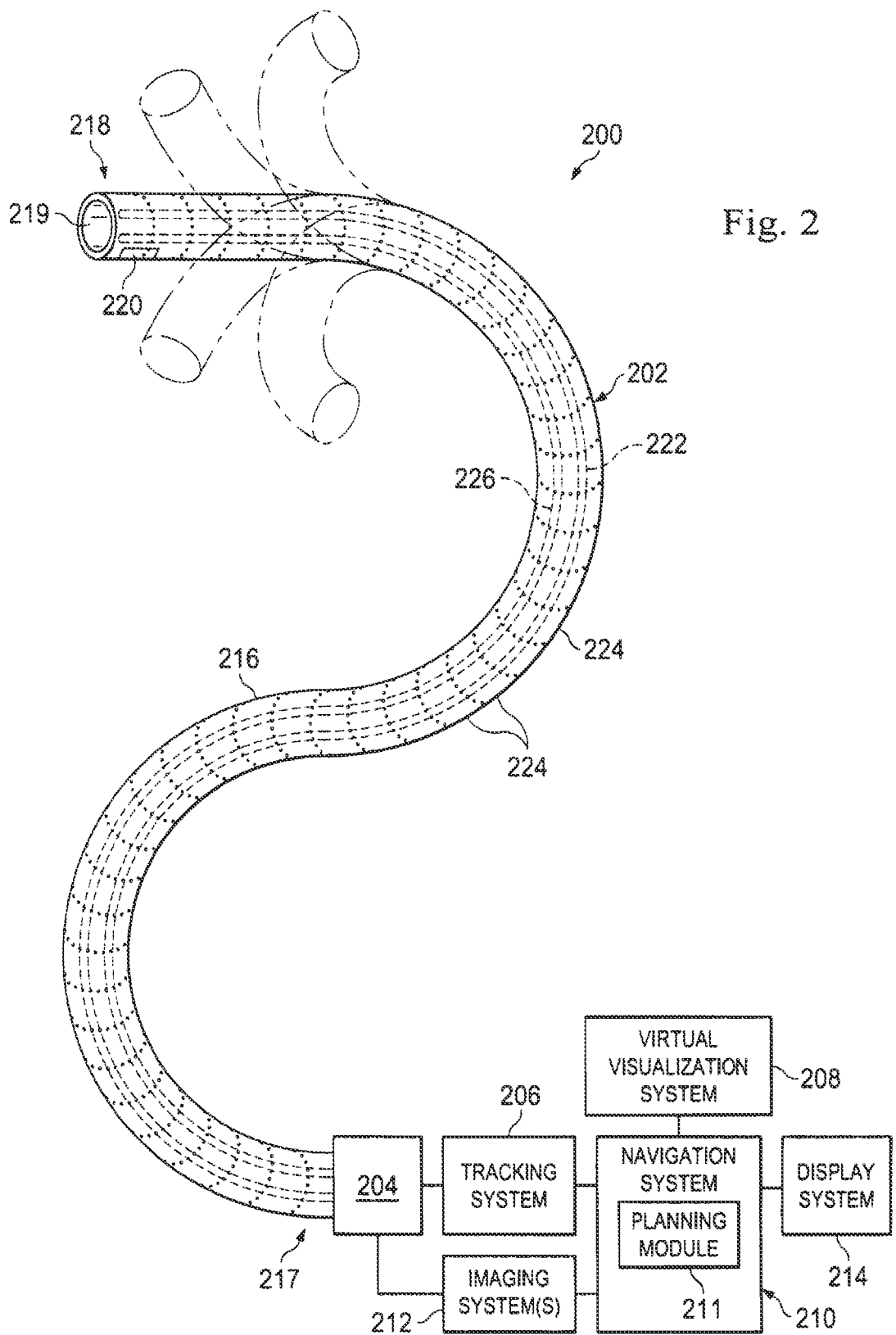
FIG. 2 illustrates an interventional instrument system utilizing aspects of the present disclosure.

FIG. 2 illustrates a minimally invasive system 200 utilizing aspects of the present disclosure. The system 200 may be incorporated into a teleoperated interventional system, such as system 100. Alternatively, the system 200 may be used for exploratory procedures or in procedures involving traditional manually operated interventional instruments, such as laparoscopic instruments. The system 200 includes a catheter system 202 (e.g., part of the instrument 104) coupled by an interface unit 204 to a tracking system 206. A navigation system 210 (e.g., part of the control system 116) processes information from a virtual visualization system 208, one or more imaging systems 212, and/or the tracking system 206 to generate one or more image displays on a display system 214 (e.g., part of the display system 111). The system 200 may further include optional operation and support systems (not shown) such as illumination systems, steering control systems, irrigation systems, and/or suction systems.

The catheter system 202 includes an elongated flexible body 216 having a proximal end 217 and a distal end 218. A channel 219 extends within the flexible body 216. In one embodiment, the flexible body 216 has an approximately 3 mm outer diameter. Other flexible body outer diameters may be larger or smaller. The catheter system 202 optionally includes a sensor system which includes a position sensor system 220 (e.g., an electromagnetic (EM) sensor system) and/or a shape sensor system 222 for determining the position, orientation, speed, pose, and/or shape of the catheter tip at distal end 218 and/or of one or more segments 224 along the body 216. The entire length of the body 216, between the distal end 218 and the proximal end 217 may be effectively divided into the segments 224. The position sensor system 220 and the shape sensor system 222 interface with the tracking system 206. The tracking system 206 may be implemented as hardware, firmware, software or a combination thereof which interact with or are otherwise executed by one or more computer processors, which may include the processors of a control system 116.

The position sensor system 220 may be an EM sensor system that includes one or more conductive coils that may be subjected to an externally generated electromagnetic field. Each coil of the EM sensor system 220 then produces an induced electrical signal having characteristics that depend on the position and orientation of the coil relative to the externally generated electromagnetic field. In one embodiment, the EM sensor system may be configured and positioned to measure six degrees of freedom. e.g., three position coordinates X, Y, Z and three orientation angles indicating pitch, yaw, and roll of a base point. Further description of an EM sensor system is provided in U.S. Pat. No. 6,380,732, filed Aug. 11, 1999, disclosing "Six-Degree of Freedom Tracking System Having a Passive Transponder on the Object Being Tracked." which is incorporated by reference herein in its entirety.

The shape sensor system 222 includes an optical fiber aligned with the flexible body 216 (e.g., provided within an interior channel (not shown) or mounted externally). The tracking system 206 may be coupled to a proximal end of the optical fiber. In one embodiment, the optical fiber has a diameter of approximately 200 μm. In other embodiments, the dimensions may be larger or smaller.

The optical fiber of the shape sensor system 222 forms a fiber optic bend sensor for determining the shape of the catheter system 202. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389, filed Jul. 13, 2005, disclosing "Fiber optic position and shape sensing device and method relating thereto;" U.S. Provisional Pat. App. No. 60/588,336, filed on Jul. 16, 2004, disclosing "Fiber-optic shape and relative position sensing;" and U.S. Pat. No. 6,389,187, filed on Jun. 17, 1998, disclosing "Optical Fibre Bend Sensor." which are incorporated by reference herein in their entireties. In other alternatives, sensors employing other strain sensing techniques such as Rayleigh scattering, Raman scattering, Brillouin scattering, and Fluorescence scattering may be suitable. In other alternative embodiments, the shape of the catheter may be determined using other techniques. For example, if the history of the catheter's distal tip pose is stored for an interval of time that is smaller than the period for refreshing the navigation display or for alternating motion (e.g., inhalation and exhalation), the pose history can be used to reconstruct the shape of the device over the interval of time. As another example, historical pose, position, or orientation data may be stored for a known point of an instrument along a cycle of alternating motion, such as breathing. This stored data may be used to develop shape information about the catheter. Alternatively, a series of positional sensors, such as EM sensors, positioned along the catheter can be used for shape sensing. Alternatively, a history of data from a positional sensor, such as an EM sensor, on the instrument during a procedure may be used to represent the shape of the instrument, particularly if an anatomical passageway is generally static. Alternatively, a wireless device with position or orientation controlled by an external magnetic field may be used for shape sensing. The history of its position may be used to determine a shape for the navigated passageways.

In this embodiment, the optical fiber may include multiple cores within a single cladding. Each core may be single-mode with sufficient distance and cladding separating the cores such that the light in each core does not interact significantly with the light carried in other cores. In other embodiments, the number of cores may vary or each core may be contained in a separate optical fiber.

In some embodiments, an array of FBG's is provided within each core. Each FBG comprises a series of modulations of the core's refractive index so as to generate a spatial periodicity in the refraction index. The spacing may be chosen so that the partial reflections from each index change add coherently for a narrow band of wavelengths, and therefore reflect only this narrow band of wavelengths while passing through a much broader band. During fabrication of the FBG's, the modulations are spaced by a known distance, thereby causing reflection of a known band of wavelengths. However, when a strain is induced on the fiber core, the spacing of the modulations will change, depending on the amount of strain in the core. Alternatively, backscatter or other optical phenomena that vary with bending of the optical fiber can be used to determine strain within each core.

Thus, to measure strain, light is sent down the fiber, and characteristics of the returning light are measured. For example, FBG's produce a reflected wavelength that is a function of the strain on the fiber and its temperature. This FBG technology is commercially available from a variety of sources, such as Smart Fibres Ltd. of Bracknell, England. Use of FBG technology in position sensors for teleoperational surgery is described in U.S. Pat. No. 7,930,065, filed Jul. 20, 2006, disclosing "Robotic Surgery System Including Position Sensors Using Fiber Bragg Gratings," which is incorporated by reference herein in its entirety.

When applied to a multicore fiber, bending of the optical fiber induces strain on the cores that can be measured by monitoring the wavelength shifts in each core. By having two or more cores disposed off-axis in the fiber, bending of the fiber induces different strains on each of the cores. These strains are a function of the local degree of bending of the fiber. For example, regions of the cores containing FBG's, if located at points where the fiber is bent, can thereby be used to determine the amount of bending at those points. These data, combined with the known spacings of the FBG regions, can be used to reconstruct the shape of the fiber. Such a system has been described by Luna Innovations. Inc. of Blacksburg, Va.

As described, the optical fiber may be used to monitor the shape of at least a portion of the catheter system 202. More specifically, light passing through the optical fiber is processed by the tracking system 206 for detecting the shape of the catheter system 202 and for utilizing that information to assist in surgical procedures. The tracking system 206 may include a detection system for generating and detecting the light used for determining the shape of the catheter system 202. This information, in turn, in can be used to determine other related variables, such as velocity and acceleration of the parts of an interventional instrument. The sensing may be limited only to the degrees of freedom that are actuated by the teleoperational system, or may be applied to both passive (e.g., unactuated bending of the rigid members between joints) and active (e.g., actuated movement of the instrument) degrees of freedom.

The flexible body 216 may optionally house one or more image capture probes 226 that transmit captured image data to the imaging system(s) 212. For example, the image capture probe 226 may be an endoscopic probe including a tip portion with a stereoscopic or monoscopic camera disposed near the distal end 218 of the flexible body 216 for capturing images (including video images) that are transmitted to the imaging system 212. The image capture probe 226 may include a cable coupled to the camera for transmitting the captured image data. Alternatively, the image capture instrument may be a fiber-optic bundle, such as a fiberscope, that couples to the imaging system. The image capture instrument may be single or multi-spectral, for example capturing image data in the visible spectrum, or capturing image data in the visible and infrared or ultraviolet spectrums.

Additionally or alternatively, the image capture probe 226 may be a sensor probe for use with a reflective imaging technology such as ultrasound or optical coherence tomography (OCT). For example, the probe may include a transmitter and receiver arrangement, such as an ultrasound transducer. The ultrasonic transducer can be mounted at an end of an elongated shaft. Such a source can be used to obtain a preoperative or intraoperative two-dimensional or three-dimensional image, or model, of the anatomic region where the interventional procedure is to be performed. As a two-dimensional source, the ultrasonic transducer can be used to obtain a single ultrasound image. As a three-dimensional source it can be used to obtain a plurality of spaced ultrasonic images, or cuts, thereby to provide sufficient information for construction of a three-dimensional model. Accordingly, it can be arranged to move, including rotate, within an anatomic site to capture such images, or cuts. This can typically be achieved, for example, in accordance with a pre-programmed sequence for moving the ultrasound transducer by teleoperational control, manual movement of the ultrasound transducer, or the like.

The body 216 may also house cables, linkages, or other steering controls (not shown) that extend between the interface 204 and the tip distal end 218 to controllably bend or turn the distal end 218 as shown for example by the dotted line versions of the distal end. The catheter system may be steerable or, alternatively, may be non-steerable with no integrated mechanism for operator control of the instrument bending. The flexible body 216 may further house control mechanisms (not shown) for operating a surgical end effector or another working distal part that is manipulable for a medical function, e.g., for effecting a predetermined treatment of a target tissue. For instance, some end effectors have a single working member such as a scalpel, a blade, an optical fiber, or an electrode. Other end effectors may include pair or plurality of working members such as forceps, graspers, scissors, or clip appliers, for example. Examples of electrically activated end effectors include electrosurgical electrodes, transducers, sensors, and the like.

Figure 3:
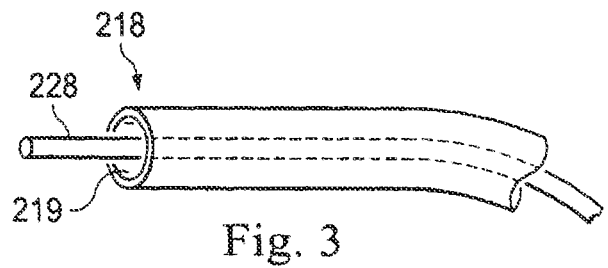
FIG. 3 illustrates a distal end of the interventional instrument system of FIG. 2 with an extended interventional tool.

As shown in greater detail in FIG. 3, interventional tool(s) 228 for such procedures as surgery, biopsy, ablation, illumination, irrigation, or suction can be deployed through the channel 219 of the and used at a target location within the anatomy. The intervertebral tool 228 may also be the image capture probe. The tool 228 may be advanced from the opening of the channel 219 to perform the procedure and then retracted back into the channel when the procedure is complete. The interventional tool 228 may be removed from the proximal end 217 of the catheter flexible body or from another optional instrument port (not shown) along the flexible body.

The virtual visualization system 208 provides navigation assistance to the catheter system 202. Virtual navigation using the virtual visualization system is based upon reference to an acquired dataset associated with the three dimensional structure of the anatomical passageways. More specifically, the virtual visualization system 208 processes images of the surgical site recorded and/or modeled using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, or the like. Software is used to convert the recorded images into a two dimensional or three dimensional model of a partial or an entire anatomical organ or anatomical region. The model describes the various locations and shapes of the passageways and their connectivity. The images used to generate the model may be recorded preoperatively or intra-operatively during a clinical procedure. In an alternative embodiment, a virtual visualization system may use standard models (i.e., not patient specific) or hybrids of a standard model and patient specific data. The model and any virtual images generated by the model may represent the static posture of a deformable anatomic region during one or more phases of motion (e.g., during an inspiration/expiration cycle of a lung).

During a virtual navigation procedure, the sensor systems may be used to compute an approximate location of the instrument with respect to the patient anatomy. The location can be used to produce both macro-level tracking images of the patient anatomy and virtual internal images of the patient anatomy. Various systems for using fiber optic sensors to register and display an interventional implement together with preoperatively recorded surgical images, such as those from a virtual visualization system, are known. For example U.S. patent application Ser. No. 13/107,562, filed May 13, 2011, disclosing, "Medical System Providing Dynamic Registration of a Model of an Anatomical Structure for Image-Guided Surgery." which is incorporated by reference herein in its entirety, discloses one such system.

The navigation system 210, as part of the control system 116, processes information from the virtual visualization system 208, the one or more imaging systems 212, and/or the tracking system 206 to determine a navigational path for the interventional instrument through the anatomical system to the target anatomical structure. The navigation system 210 may also monitor the navigational path of the interventional instrument as it moves through the anatomical system to a target structure. The navigation system 210 includes a planning module 211 that allows a clinician to locate a target anatomical structure (e.g., a tumor) in the anatomical model prepared by the virtual visualization system 208 and to identify a navigational path through anatomical passageways to reach the target structure to perform an interventional procedure (e.g., a biopsy) with the interventional instrument. The target localization and navigational path determination may be automated such that the navigation system identifies one or more navigational paths. Alternatively, a clinician may determine the navigational path from the anatomic model and optionally communicate the selected path to the navigational system. In still another alternative, the planning module uses a hybrid automated/clinician selected navigational path determination in which the clinician may modify a system planned path or in which the clinician may enter parameters such as anatomical areas to avoid or instrument limitations that constrain the planned navigational path suggested by the planning module 212.

Figure 4:
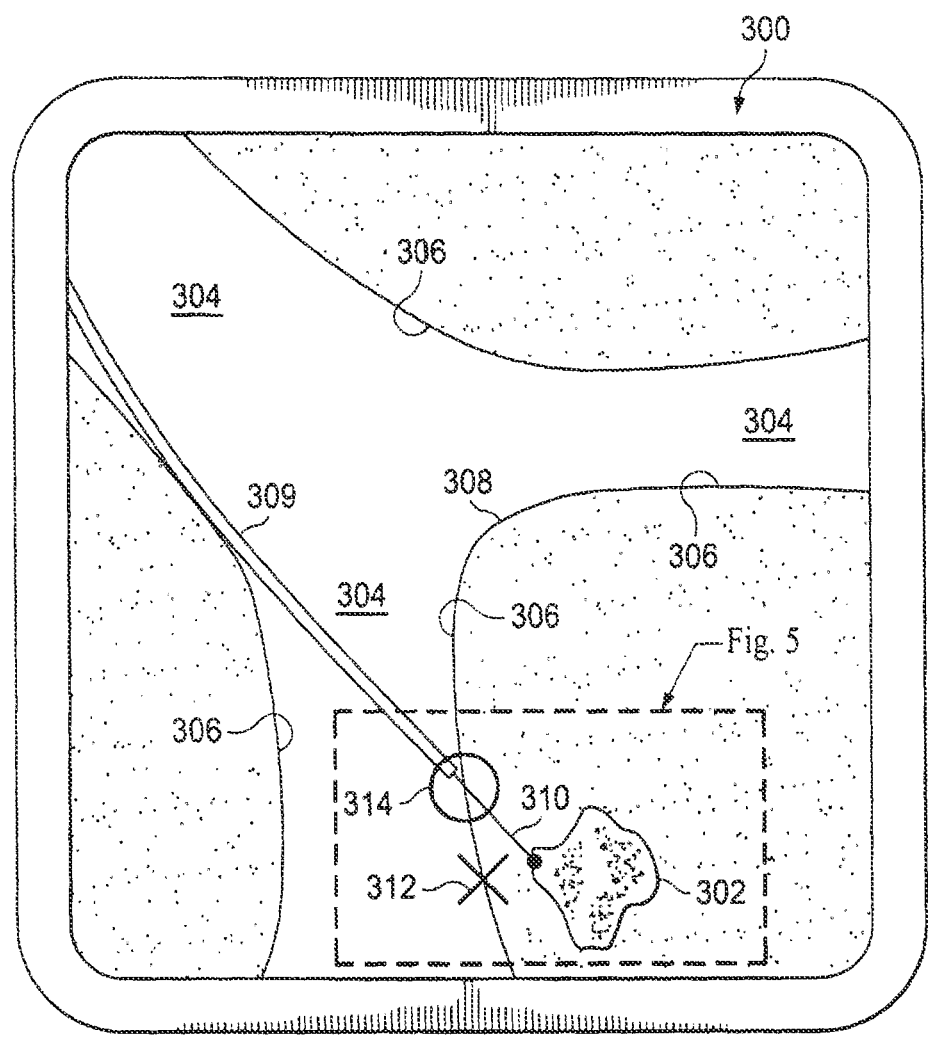
FIG. 4 illustrates an anatomic model image with a distal end of an interventional instrument at a deployment location.

The navigation planning module generates or allows the clinician to select a planned deployment location within an anatomical passageway for parking a distal end of the interventional instrument to conduct the interventional procedure. Referring now to FIG. 4, a virtual image 300 of target structure 302, such as a tumor, and nearby anatomic passageways 304 is depicted. The passageways include passageway walls 306 and carina 308. In this embodiment, the anatomic passageways are bronchial passageways of the lung, but the systems and methods of this disclosure may be suitable for use in other natural or surgically created passageways in anatomical systems such as the colon, the intestines, the kidneys, the heart, or the circulatory system. An interventional instrument with a flexible body 309 (substantially similar to flexible body 216) and an extended interventional tool 310 are shown. In one embodiment, a navigation planning module identifies the planned deployment location as a location 312 along a wall of an anatomic passageway closest to or nearby to the target structure. However, selecting the deployment location entirely on the basis of proximity to the target structure may result in a selected deployment location that is inaccessible or not easily accessible by the interventional instrument. For example, the interventional instrument may be incapable of bending sufficiently within the passageway to access the proximity based deployment location. Additionally the selected deployment location or the navigational path to the deployment location may not consider anatomical constraints, such as scar or diseased tissue to avoid.

In other embodiments, a navigation planning module selects the deployment location based upon a plurality of factors, which in some instances may be procedural characteristics, such as the distance to the target structure, and/or the position of the target structure relative to other anatomic features. In other embodiments, the navigation planning module may additionally or alternatively receive and use information about the operational capability of the interventional instrument to determine a deployment location. For example, information pertaining to the bending capability of the instrument may be considered, such as the flexibility and elasticity of the catheter material, any preformed shape characteristics of the catheter or tools passed through the channel of the catheter, the steerability of the distal end of the catheter or tool (e.g., the degree to which the distal tip of the catheter may be curved relative to the main axis of the catheter), and the curvature along the length of the catheter. Other characteristics of the interventional instrument may also be used to determine the deployment location including the diameter of the catheter, the diameter of the tool, the trajectory of the tool when extended from the catheter (e.g., curved, straight), the movement of the tool (e.g., sweeping, spinning, linear), the maximum angulation of the axis of the tool versus the axis of the catheter, the maximum length the tool can be extended from the catheter, and any anchoring structures at the distal tip of the catheter providing frictional contact with the passageway wall. The information pertaining to the bending capability and/or the information related to the characteristics of the interventional instrument are exemplary factors that can be used to determine the operational capability of the interventional instrument within the anatomical passageways.

The navigation planning module may also or alternatively receive and use information about the patient anatomy to determine a deployment location. Such information may include, for example, the location of the carinas of the anatomical passageways nearest to the target structure and the size of the passageways nearest to the target structure. Other anatomic information may include the elasticity of the anatomical passageways including the impact that any disease processes may have had on the elasticity of the passageways. The navigation planning model may also consider the surrounding anatomic tissue to, for example, select a deployment location that reduces the risk to surrounding tissue. As one example, a deployment location away from the perimeter of a lung may be selected to avoid the risk of puncturing the lung with the deployed tool. The navigation planning model may also consider the anatomy of the target structure to access a preferred location of the target structure. For example, the deployment location may be selected such that a biopsy tool avoids a calcified part of a tumor.

The navigation planning module may also consider information about the relationship between the interventional instrument and the patient anatomy such as the distance of the target structure from the end of the catheter. Referring to FIG. 5, the navigation planning module may also consider the angle of approach 320 between the interventional tool and the passageway wall. For example, an approach angle of 90° may impracticable due to the small size of the passageway and the bendability of the distal tip of the catheter. An approach angle of 1° may also be unsuitable because of the risk that the interventional tool may graze the surface of the passageway wall without penetrating. For these reasons, the navigation planning module may select a deployment location such that the approach angle is between approximately 30° and 90°.

Referring again to FIG. 4, after the navigation planning module evaluates the factors related to the interventional instrument and the patient anatomy, a deployment location 314 on the wall of an anatomic passageway is identified. Optionally, the navigation planning module may provide a suggested navigational path to the deployment location. The clinician can then direct the distal end of the interventional instrument to the deployment location. The clinician may manually control the navigation of the interventional instrument based upon virtual or real image guidance. Alternatively, the clinician can teleoperationally control the navigation of the interventional instrument or allow computer-controlled navigation of the interventional instrument along the suggested navigational path. After the distal end of the interventional instrument is positioned at the deployment location, the interventional tool is extended from the catheter, through the passageway wall and into contact with the target structure. In some circumstances, for example when a target structure is located within an anatomic passageway, the deployment location may be located within the lumen of the passageway, rather than on the wall of the passageway. For example when the target structure is within the passageway, the deployment location may be on a surface of the target structure.

FIG. 7 is a flowchart describing a method 400 used by the navigation planning module for identifying a planned deployment location for an interventional instrument. At 402, a model of an anatomic structure is received. The anatomic structure includes a plurality of anatomic passageways which are illustrated by the model. The model is formed from two or three dimensional images of the surgical site recorded and/or modeled preoperatively or interoperatively using imaging technology such as CT, MRI, fluoroscopy, thermography, ultrasound, OCT, thermal imaging, impedance imaging, laser imaging, nanotube X-ray imaging, or the like. Receipt of the model may include receiving information about the patient anatomy derived from the model, from user inputs describing the patient anatomy, or from other reference sources. Such information about the patient anatomy may include, for example, the closest location(s) within an anatomic passageway(s) to the target structure, the location of the carinas of the anatomical passageways nearest to the target structure, and the size of the passageways nearest to the target structure. Other anatomic information may include the elasticity of the anatomical passageways, the anatomy of the target structure to access a preferred location of the target structure, and the type of surrounding tissue and any risk associated with contacting the surrounding tissue.

At 404, a location of a target structure (e.g., a tumor) is identified in the model. Identifying the target structure may include determining or receiving information about the target structure from the model, from user inputs describing the target structure, or from other reference sources. Such information about the target structure may include, for example, the shape of the target structure, the one or more substances that form the target structure, and the location of the surfaces of the target structure relative to nearby anatomic passageways.

At 406, information about the operational capability of the interventional instrument is received. The information received to determine the operational capability of the interventional instrument may include, for example, information pertaining to the bending capability of the instrument such as the flexibility and elasticity of the catheter material, any preformed shape characteristics of the catheter or tools passed through the channel of the catheter, the steerability of the distal end of the catheter or tool, and the curvature along the length of the catheter. The operational capability of the interventional instrument may also be determined from characteristics of the interventional instrument such as the diameter of the catheter, the diameter of the tool, the maximum angulation of the axis of the tool versus the axis of the catheter, the maximum length the tool can be extended from the catheter, and any anchoring structures at the distal tip of the catheter providing frictional contact with the passageway wall.

At 408, a planned deployment location for the interventional instrument is located. The planned deployment location may be marked on the model of the plurality of passageways. The planned deployment location can be selected based upon the instrument operational capability information, the target structure information, the patient anatomy information, or a combination of the types of information. The selected deployment location may be at a point in an anatomic passageway nearest to the target structure. However, in many patients a nearest point deployment location may be impossible for the distal end of the interventional instrument to reach because the instrument has insufficient bend capability within the size and elasticity constraints of the selected anatomic passageway. A more suitable deployment location may be at a point on an anatomic passageway wall where the interventional instrument has an approach angle to the passageway wall that is within the bending capability of the instrument. For example, if the interventional instrument has an inflexible distal end that permits little or no bending, a suitable deployment location may be at a carina near the target structure. At the carina the interventional instrument may be deployed at an approximately 90° approach angle to the passageway wall with minimal bending of the distal end of the instrument. As another example, the navigation planning module may select a deployment location such that the approach angle is between approximately 30° and 90°. When selecting a deployment location, the planning system also confirms that the interventional tool is capable of extending from the catheter a sufficient distance to reach the target structure to perform the interventional procedure.

As described, the planned deployment location may be located based on the analysis of the instrument operational capability, the target structure, and the patient anatomy. Alternatively or in combination with the system assessment, the planned deployment location may be identified by a clinician and communicated to the navigation planning module to locate or mark the clinician-identified planned deployment location in the model. When the navigation planning module receives the clinician-identified planned deployment location, the module may compare it with the system-identified deployment location. A visual or audible feedback cue may be issued if the clinician-identified deployment location is objectionable (e.g., "The chosen biopsy needle is not long enough to reach the target from this deployment location.").

Optionally, the navigation planning module identifies multiple elective deployment locations. The elective deployment locations may be coded (e.g., with color on the display) to provide information about the relative quality of the elective deployment locations for deploying the interventional instrument to perform the procedure. A clinician may select one of elective deployment locations to be the planned deployment location. Alternatively, more than one planned deployment location may be selected from the elective deployment locations, allowing the interventional procedure to be performed from different approaches. The selection of elective deployment locations may also occur during the interventional procedure if the clinician determines that an initially chosen deployment location is unsuitable.

Figure 6:
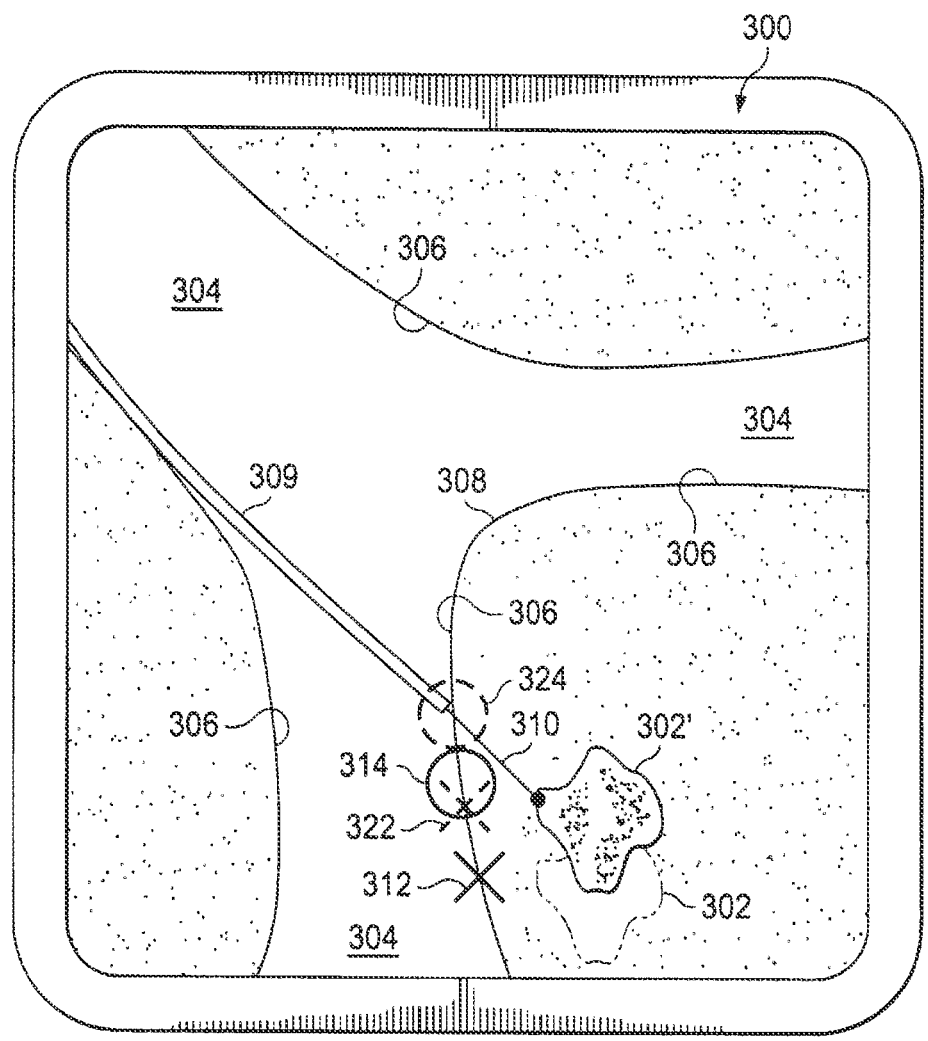
FIG. 6 illustrates an anatomic model image with a distal end of an interventional instrument at a revised deployment location based on sensor feedback.

To further refine the step of identifying the target structure, one or more of the imaging systems 212 may be used to gather additional information about the location of the target structure after the interventional instrument has been deployed to the identified deployment location or the general vicinity thereof. Referring now to FIG. 6, the virtual image 300 of target structure 302 and nearby anatomic passageways 304 is again depicted. The distal end of the flexible body 309 is first positioned at a target confirmation location such as location 312. The image capture probe 226 is operated to determine if the target structure 302 is in the expected position relative to the target confirmation location. If the target structure 302 is not found or not in the expected position, the flexible body and image capture probe can be moved around until the target structure is located. When the target structure is located, the location of the distal end of the flexible body 309 or image capture probe is recorded at a new location 322. The navigation planning module 211 then updates the location of the target structure 302'. With the new location of the target structure identified, the operational capability information for the interventional instrument is used to identify a revised planned deployment location 324. For example, the navigation planning module may use the difference between locations 312 and 322 to update location 314 to location 322 and to update the location of the target structure 302 to 302'. In one embodiment, the image capture probe uses one or more sensors for reflective imaging technology such as ultrasound or OCT to refine the location of the target structure. Alternatively, other non-imaging sensors may be used to identify the location of the target structure.

FIG. 8 is a flowchart describing a method 450 used by the navigation planning module for revising a planned deployment location for an interventional instrument. At 452, information is received from the image capture probe after the probe has been operated at the initial planned deployment location or at a target confirmation location. At 454, a revised location of the target structure is identified using the information received from the image capture probe. At 456, a revised planned deployment location is identified in the model of the plurality of passageways.

An alternative method 500 for identifying the target structure using the imaging systems 212 is described at FIG. 9 and illustrated at FIGS. 10A, 10B, and 11. The method 500 may be performed to identify an initial interventional deployment location or may be used to identify a revised deployment location as described below.

At 502, the catheter is navigated to a passageway location such as location 312 or 314 with the guidance of the navigation system including, for example, visual. EM or shape sensor information. A confirmation from the clinician or from the interventional instrument may be provided when the catheter has reached the location. At 504, an imaging probe (e.g., an ultrasound probe) is inserted through the catheter and the movement of the imaging probe relative to a portion of the catheter (e.g., the catheter tip) is tracked. In some embodiments, the same imaging probe (e.g., the same ultrasound probe) could also be used during the navigation of 502. The movement of the imaging probe may be tracked, for example using a positional sensor such as a 5 or 6 degree of freedom EM sensor. Alternatively, the movement may be tracked using an insertion sensor such as an encoder located outside the patient anatomy. Alternatively, the movement may be tracked by engaging a stepping motor to control the insertion motion of the imaging probe.

At 506, the roll angle of an imaging coordinate system for the imaging probe is determined with respect to the catheter. For example, the roll angle may be determined using a roll alignment feature of the axial imaging probe and the catheter (e.g. a key system). Alternatively, a roll sensor located outside of the patient anatomy may be used. In still another alternative, the roll angle may be determined by viewing one or more markers or other features with a known angle relative to the catheter in the image recorded by the imaging probe. For example, the feature or marker may be located on the circumference of the catheter and have a contrast (e.g. an ultrasound contrast) to the catheter.

At 508, the catheter and/or the imaging probe is moved around in the anatomic passageways to detect the target structure in the image generated by the probe. At 510, after the target structure is detected by the imaging probe, a clinician may identify the target structure in the image using a pointing device at a pointer location. The image (e.g. an ultrasound image) may be generated by a scan that is gated for respiratory and/or cardiac cycles. A three-dimensional image may be constructed from two-dimensional scans.

At 512, the pointer location is transformed to the catheter coordinate system or to the patient coordinate system (which has been previously registered to the catheter coordinate system). At 514, the pointer location can be used to apply an offset to the location of the target structure identified in the preoperative anatomic model. A revised target structure location is computed based upon the offset. The imaging probe may then be removed and a biopsy tool or other interventional tool may be inserted through the catheter to perform a procedure (e.g., a biopsy) at the revised location.

FIG. 10A illustrates a patient reference frame indicated with the coordinate references $X_P$, $Y_P$, and $Z_P$. Also illustrated is a catheter C having a catheter tip reference frame indicated with the coordinate references $X_C$, $Y_C$, and $Z_C$. A target location $P_P$ is shown in the patient reference frame. A target location Q according to the pre-op model is shown. A correction vector O between the target locations Q and $P_P$ is also shown. A tracked insertion length L from the catheter tip is shown.

FIG. 10B is an ultrasound image having an image reference frame indicated with the coordinate references $X_I$, $Y_I$, and $Z_I$. A target location $P_I$ is shown in the image reference frame.

FIG. 11 illustrates a biopsy procedure according to $P_P$ instead of Q, using biopsy instrument B.

Although the systems and methods of this disclosure have been described for use in the connected bronchial passageways of the lung, they are also suited for navigation and treatment of other tissues, via natural or surgically created connected passageways, in any of a variety of anatomical systems including the colon, the intestines, the kidneys, the brain, the heart, the circulatory system, or the like. The methods and embodiments of this disclosure are also suitable for non-interventional applications.

One or more elements in embodiments of the invention may be implemented in software to execute on a processor of a computer system such as control system 116. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet, Intranet, etc.

Note that the processes and displays presented may not inherently be related to any particular computer or other apparatus. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A system for performing an interventional procedure, the system comprising:
   an interventional instrument comprising a catheter and an interventional tool extendable from the catheter; and
   a control system comprising a processor and a memory comprising machine-readable instructions that, when executed by the processor, cause the control system to:
   receive a model of an anatomic structure, the anatomic structure including a plurality of passageways;
   identify a target structure in the model;
   receive information about a maximum extension length the interventional tool can be extended relative to a distal tip of the catheter;
   based upon the received information about the maximum extension length, identify a planned deployment location for positioning the distal tip of the catheter to perform the interventional procedure on the target structure;
   determine a navigational path for the catheter to the target structure; and
   navigate the catheter to the identified planned deployment location via computer-control or based on user input.

2. The system of claim 1, wherein the interventional tool comprises an imaging probe.

3. The system of claim 2, wherein the imaging probe comprises an ultrasound probe.

4. The system of claim 2, wherein the imaging probe comprises an optical coherence tomography probe.

5. The system of claim 1, wherein the machine-readable instructions, when executed by the processor, further cause the control system to track movement of the interventional tool relative to the catheter based on a motor used to control insertion of the interventional tool.

6. The system of claim 1, wherein the machine-readable instructions, when executed by the processor, further cause the control system to track movement of the interventional tool relative to the catheter using an electromagnetic positional sensor.

7. The system of claim 1, wherein the machine-readable instructions, when executed by the processor, further cause the control system to issue a feedback cue indicating a user-identified planned deployment location based on a user input is objectionable.

8. The system of claim 7, wherein the interventional tool comprises a biopsy needle, and wherein the user-identified planned deployment location is determined to be objectionable based on a determination that the biopsy needle cannot reach the target structure from the user-identified planned deployment location.

9. The system of claim 1, wherein the instructions, when executed by the processor, cause the control system to:
   receive user input to move the catheter, wherein navigating the catheter to the planned deployment location is based on the received user input.

10. A system for performing an interventional procedure, the system comprising:
    an interventional instrument comprising a catheter and an interventional tool extendable from the catheter; and
    a control system comprising a processor and a memory comprising, machine-readable instructions, that when executed by the processor, cause the control system to:
    receive a model of an anatomic structure, the anatomic structure including a plurality of passageways;
    identify a target structure in the model;
    receive information about a maximum extension length the interventional tool can be extended relative to a distal tip of the catheter;

based upon the received information about the maximum extension length, identify a planned deployment location for positioning the distal tip of the catheter to perform the interventional procedure on the target structure; and track movement of the interventional tool relative to the catheter using an insertion sensor.

11. The system of claim 10, wherein the insertion sensor comprises an encoder.

12. A method of planning an interventional procedure by a control system, the method comprising:

receiving a model of an anatomic structure, the anatomic structure including a plurality of passageways;

identifying a target structure in the model;

receiving information about a maximum extension length an interventional tool can be extended relative to a distal tip of a catheter;

based upon the received information about the maximum extension length, identifying a planned deployment location for positioning the distal tip of the catheter to perform the interventional procedure on the target structure;

determining a navigational path for the catheter to the target structure; and navigating the catheter to the identified planned deployment location via computer-control or based on user input.

13. The method of claim 12, further comprising:

receiving image data captured by an imaging system; and based upon the information received about the maximum extension length of the interventional tool and the image data, identifying a plurality of optional deployment locations for positioning the distal tip of the catheter to perform the interventional procedure on the target structure.

14. The method of claim 13, further comprising:

displaying the plurality of optional deployment locations in the model on a display system, wherein each of the plurality of optional deployment locations is displayed with an indication of a relative quality of each respective optional deployment location, the relative quality of each of the plurality of optional deployment locations based on the information received about the maximum extension length.

15. The method of claim 12, wherein the interventional tool comprises an imaging probe.

16. The method of claim 12, further comprising tracking movement of the interventional tool relative to the catheter using an insertion sensor.

17. The method of claim 16, wherein the insertion sensor comprises an encoder.

18. The method of claim 12, further comprising tracking movement of the interventional tool relative to the catheter based on a motor used to control insertion of the interventional tool.

19. The method of claim 12, further comprising tracking movement of the interventional tool relative to the catheter using an electromagnetic positional sensor.

20. The method of claim 12, further comprising issuing a feedback cue indicating a user-identified planned deployment location based on a user input is objectionable.

21. The method of claim 20, wherein the interventional tool comprises a biopsy needle, and wherein the user-identified planned deployment location is determined to be objectionable based on a determination that the biopsy needle cannot reach the target structure from the user-identified planned deployment location.

* * * * *